United States Patent
Brüggemann et al.

(10) Patent No.: US 9,572,927 B2
(45) Date of Patent: Feb. 21, 2017

(54) MEDICAMENT DELIVERY DEVICES (75) Inventors: Ulrich Brüggemann, Frankfurt am Main (DE); Christopher Jones, Gloucestershire (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 496 days.

(21) Appl. No.: 13/147,853

(22) PCT Filed: Feb. 3, 2010

(86) PCT No.: PCT/EP2010/051275
§ 371 (c)(1),
(2), (4) Date: Dec. 23, 2011

(87) PCT Pub. No.: WO2010/089313
PCT Pub. Date: Aug. 12, 2010

(65) Prior Publication Data
US 2012/0172817 A1 Jul. 5, 2012

(30) Foreign Application Priority Data

Feb. 5, 2009 (EP) .................................. 09001578

(51) Int. Cl.
*A61M 5/145* (2006.01)
*A61M 5/142* (2006.01)
*A61M 5/315* (2006.01)

(52) U.S. Cl.
CPC .................. *A61M 5/14566* (2013.01); *A61M 2005/14268* (2013.01); *A61M 2005/3152* (2013.01); *A61M 2005/31518* (2013.01)

(58) Field of Classification Search
CPC .... A61M 2005/31518; A61M 5/14566; A61M 5/315; A61M 5/145;
(Continued)

(56) References Cited

U.S. PATENT DOCUMENTS 7,066,909 B1 * 6/2006 Peter ................. A61M 5/14244
604/134
9,149,583 B2   10/2015 Plumptre
(Continued)

FOREIGN PATENT DOCUMENTS

EP       1472477 B1    11/2005
JP     2001321440 A    11/2001
(Continued)

OTHER PUBLICATIONS

English Translation of Japanese Patent Application No. 2008-125803. Dated Jun. 27, 2012.
(Continued)

*Primary Examiner* — Bhisma Mehta
*Assistant Examiner* — Laura Schell
(74) *Attorney, Agent, or Firm* — McDonnell Boehnen Hulbert & Berghoff LLP (57) ABSTRACT

A medicament delivery device comprises a housing, a telescopic piston rod assembly for driving a bung of a medicament container, and a drive mechanism for the telescopic piston rod assembly. The telescopic piston rod assembly comprises a plunger for driving a bung, a key for allowing predominantly axial movement between the plunger and the housing and an input drive telescopically coupled to the plunger and supported for rotational and axial movement relative the housing. The drive mechanism additionally comprises a transfer drive that operates to rotate the input drive. As the input drive rotates, it moves axially relative to the housing, expanding telescopically relative to the plunger.

11 Claims, 8 Drawing Sheets

(58) Field of Classification Search
CPC ........... A61M 2005/14506; A61M 2005/3152; A61M 5/14216; A61M 5/1422; A61M 5/31511; A61M 2005/31598; A61M 5/31575; A61M 5/2429
USPC ................................ 604/218, 224, 154, 155
See application file for complete search history.

(56) References Cited

U.S. PATENT DOCUMENTS

2004/0000818 A1\* 1/2004 Preuthun et al. ............... 310/12
2005/0197650 A1 9/2005 Sugimoto et al.

FOREIGN PATENT DOCUMENTS

| JP | 2005515383 A | 5/2005 |
| JP | 2005245852 A | 9/2005 |
| JP | 2008-125803 A | 6/2008 |
| WO | 9700091 A1 | 1/1997 |
| WO | 03061736 A1 | 7/2003 |

OTHER PUBLICATIONS

English Translation of Notification of Reasons for Refusal issued in Japanese Patent Application No. 2011-548671 dated Dec. 17, 2013.

\* cited by examiner

MEDICAMENT DELIVERY DEVICES

CROSS REFERENCE TO RELATED APPLICATIONS

The present application is a 35 U.S.C. 371 National Application of PCT/EP2010/051275 filed Feb. 3, 2010, which claims priority to European Patent Application No. 09001578.5, filed Feb. 5, 2009, the entire contents of which are incorporated entirely herein by reference.

This invention relates to medicament delivery devices for delivering medicine to the human or animal body and in particular, but not exclusively, to devices having a replaceable medicament cartridge. Such devices are commonly used by those with diabetes for the administration of insulin.

Medicament delivery devices are routinely used by persons without formal medical training, i.e. patients where self-management of their condition is increasingly common. These circumstances set a number of requirements for medicament delivery devices of this kind. The injector should be robust in construction, yet easy to use in terms of its operation by a user and the manipulation of the parts. In the case of those with diabetes, many users will be of impaired vision and may also be physically infirm. Devices that are too large of cumbersome may therefore prove difficult to use, particularly someone with reduced dexterity.

Patent Specification WO 03/061736 describes a medicament injection device with an axially displaceable lead screw. In this device, the lead screw is in threaded piston engagement with a drive mechanism that comprises a gear and electric motor. The rotational drive of the motor is translated into an axial force by the gear and threaded piston, the axial force being applied to a bung or elastomeric piston of the medicament cartridge. This driving action is operative to expel an amount of the medicine from the cartridge. In order to fully empty the cartridge, the length of the lead screw has to be at least equal to the length of the cartridge, making the total length of the device at least twice the length of the cartridge. A problem with this type of injection device is that the total length is too long to fit unobtrusively into a jacket pocket or handbag.

In order to produce a device that is shorter than twice the length of the cartridge, a telescopic piston rod has been developed. Such a telescopic piston rod is shown, utilized in an infusion device, in WO 97/00091. This patent specification describes a linear-transmission syringe plunger that has a piston rod comprising a plurality of pieces or parts connected to one another by mating threads. The distal part of the telescopic piston rod is connected to the elastomeric piston of the syringe, and is prevented from rotating by a number of bushings surrounding the telescopic piston rod. The bushing of the largest diameter needs to fit within the diameter of the syringe with the consequence that the telescopic piston is only suitable for a syringe of considerable size.

It is an aim of the present invention to provide a medication delivery device that has a telescopic piston rod assembly that is more compact.

According to the present invention, there is provided a medicament delivery device comprising: a housing; a telescopic piston rod assembly for driving a bung of a medicament container; and a drive mechanism for the telescopic piston rod assembly; characterised in that:

the telescopic piston rod assembly comprises a plunger for driving the bung, a key for allowing predominantly axial movement between the plunger and the housing; and an input drive telescopically coupled to the plunger and supported for rotational and axial movement relative the housing; and the drive mechanism comprises a transfer drive operative for rotating the input drive whereby the input drive moves axially relative to the housing as the input drive moves telescopically relative to the plunger.

In a preferred embodiment, the key may allow a predetermined amount of rotational movement. The plunger is provided with an external screw thread that engages with an internal screw thread of the input drive so that rotation of the input drive telescopically moves the plunger into or out (i.e. to expand or retract the assembly) of the input drive. The input drive is also provided with an external screw thread that engages with and passes through a correspondingly screw threaded opening provided in the housing, so that rotation of the input drive moves the input drive through the opening. The input drive is also provided with a drive gear at its end opposite the internal screw thread for meshing with an axially extending gear of the transfer drive. This is so that the input drive can be rotated by the transfer drive, and that the drive gear can slide along the axially extending gear relative to the housing. The device therefore comprises three components, namely the plunger, input drive and transfer drive that extend or retract axially relative to one another. The drive mechanism also includes a battery driven motor for driving the transfer drive via a gear train.

The key may comprise an elongate member that non-rotationally extends into an end of the plunger opposite from the end thereof that drives the medicament cartridge piston. The non-rotational relationship between the key and the plunger may be achieved by a male-female spline arrangement or by forming the key ins, for example, a D-shaped cross-section that fits with a correspondingly profiled D-shaped internal cross-section of the plunger. The key extends through the input drive such that the end of the key remote from the plunger extends to the opposite side of the screw threaded opening of the housing to lie substantially alongside or adjacent to the axially extended gear of the transfer drive. This end of the key is provided with a tab or projection that extends over the drive gear of the input drive and into a corresponding recess or guide provided on or in the housing. This corresponding recess or guide is disposed parallel to the axially extending gear so that as the input drive is rotated and moves through the screw threaded opening, the key moves axially in parallel for at least part or all of the length of the axially extending gear. This ensures that the plunger does not rotate with the input drive as the latter rotates, but instead moves telescopically relative to the input drive through the relative rotation and threaded relationship between the input drive and the plunger. The tab or projection, extending over the drive gear, ensures that the key travels with the input drive in either axial direction so that the drive mechanism can expand or retract the telescopic piston rod axially.

Embodiments of the key may allow a degree of rotational movement to allow for any tolerances between the components and particularly within the gear train. Additionally, embodiments of the tab or projection provided on the end of the key may run within a non-parallel recess or guide, to allow for a degree of rotational movement.

The gear train may also feature a noise reduction device, such as a spring element, for reducing noise and/or reducing tolerances between the components of the drive mechanism.

The term "medicament delivery device" according to instant invention shall mean a single-dose or multi-dose or pre-set dose or pre-defined, disposable or re-useable device designed to dispense a user selectable or pre-defined dose of a medicinal product, preferably multiple doses, e.g. insulin, growth hormones, low molecular weight heparins, and their analogues and/or derivatives etc. Said device may be of any shape, e.g. compact or pen-type. Dose delivery may be provided through a mechanical (optionally manual) or electrical drive mechanism or stored energy drive mechanism, such as a spring, etc. Dose selection may be provided through a manual mechanism or electronic mechanism. Additionally, said device may contain components designed to monitor physiological properties such as blood glucose levels, etc. Furthermore, the said device may comprise a needle or may be needle-free. In particular, the term "medicament delivery device" may refer to a needle-based device providing multiple doses having an electrical drive mechanism, which is designed for use by persons without formal medical training such as patients. Preferably, the drug delivery device is of the automated-type, i.e. an auto-injector.

The term "housing" according to instant invention shall preferably mean any exterior housing ("main housing", "body", "shell") or interior housing ("insert", "inner body") having a unidirectional axial coupling to prevent proximal movement of specific components. The housing may be designed to enable the safe, correct, and comfortable handling of the drug delivery device or any of its mechanism. Usually, it is designed to house, fix, protect, guide, and/or engage with any of the inner components of the drug delivery device (e.g., the drive mechanism, cartridge, plunger, piston rod) by limiting the exposure to contaminants, such as liquid, dust, dirt etc. In general, the housing may be unitary or a multipart component of tubular or non-tubular shape. Usually, the exterior housing serves to house a cartridge from which a number of doses of a medicinal product may by dispensed.

The term "motor" according to the instant invention shall preferably mean any motorised means for driving the gearing system and ultimately the input drive means. In the instant invention a stepper motor is preferably utilised although any means for driving the gearing system or the drive means, including a mechanical or manual actuation means, may also be incorporated into the device.

The "proximal end" of the device or a component of the device shall mean the end, which is furthest away from the dispensing end of the device.

The "distal end" of the device or a component of the device shall mean the end, which is closest to the dispensing end of the device.

Embodiments of the present invention provide for more compact medicament delivery devices, both in terms of the axial length of the device as well as the diameter of medicament container. Consequently, devices embodying the invention may be usefully deployed in re-useable medicament delivery devices that comprise replaceable medicament cartridges and may also be deployed within an auto-injector device. Moreover, in embodiments of the present invention, the axial movement of the input drive relative to the housing is advantageously simultaneous with the telescopic movement of the plunger. This provides for the application of a constant or steady force to the piston of the medicament container during delivery of the medicament.

The invention will now be further described by way of example with reference to the accompanying drawings, in which like reference numerals designate like elements.

Figure 1:
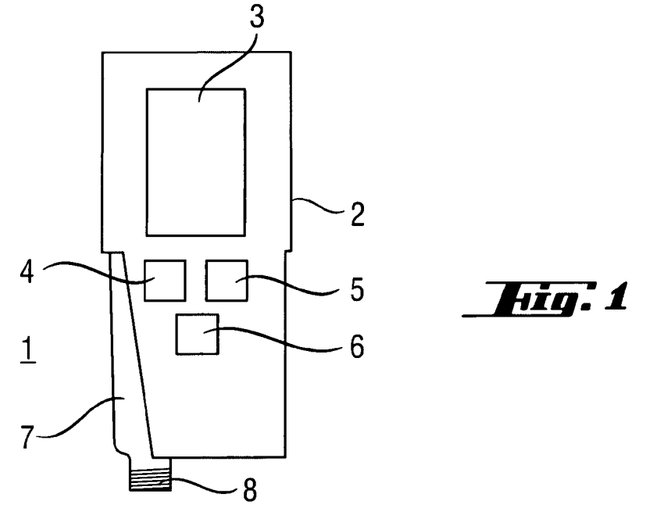
FIG. 1 is a schematic front view of a medicament delivery device embodying the present invention.
Figure 2:
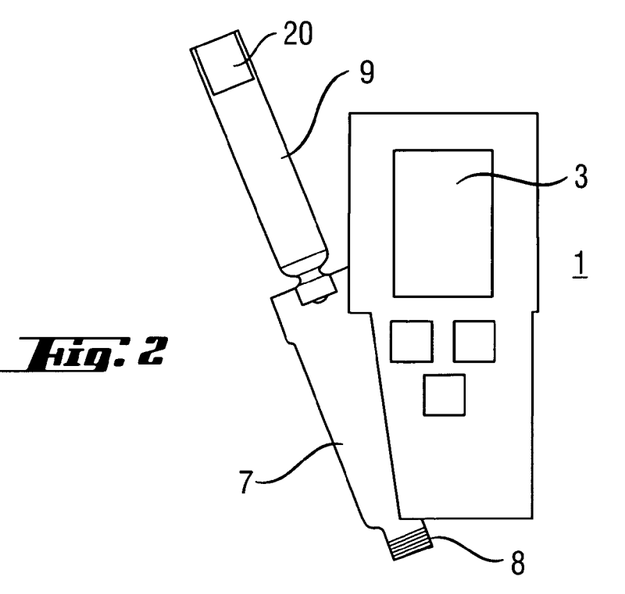
FIG. 2 is a schematic front view of the medicament delivery device of FIG. 1 with a medicament cartridge door shown in an open position for receiving a medicament cartridge.

In FIG. 1, a medicament delivery device 1 comprises a case 2 having a display 3 for displaying functional information relating to the operation of the medicament delivery device, including the set dose, number of doses remaining in the medicament cartridge. User interface buttons 4, 5 and 6 (and others, not shown) are provided to allow the user to operate the injector including priming, setting a dose, opening a medicament cartridge holder and door 7, and activating the dispensing of the set dose. A threaded needle attachment 8 is provided to which a needle can be attached for dose delivery and subsequently removed and discarded. A cover (not shown) may be provided to fit over the lower portion of the case 2 to assist in protecting the device from the ingress of particles and fluid. FIG. 2 shows the medicament delivery device 1 with the cartridge holder and door 7 in an open position for receiving a replacement medicament cartridge 9.

Figure 3:
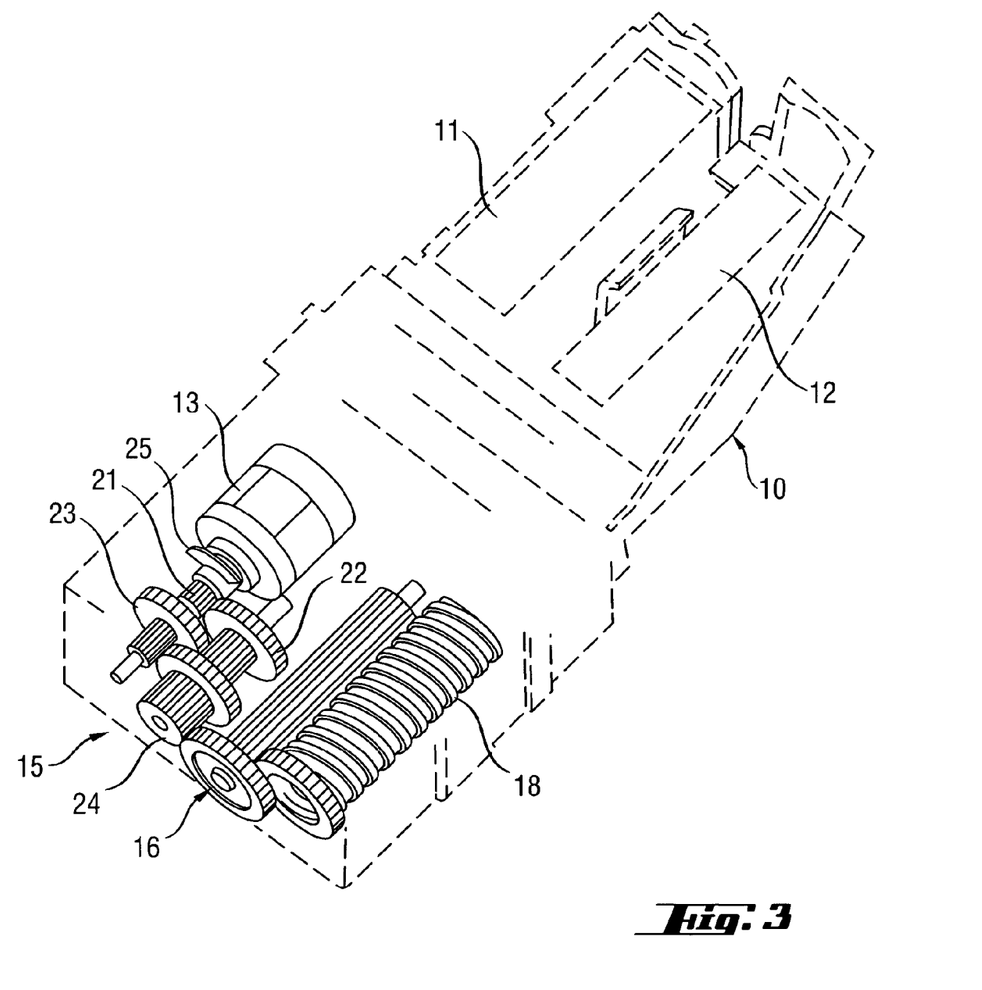
FIG. 3 is an outline perspective view of a housing for the medicament delivery device of FIGS. 1 and 2 showing a drive mechanism and part of a telescopic piston rod assembly.

FIG. 3 shows an outline of a chassis 10 of the medicament delivery device 1. The chassis comprises space 11 for a battery (not shown) and space 12 for the medicament cartridge holder and door 7. The chassis also accommodates an electric motor 13 operative for driving a drive mechanism that includes a gear train generally designated by reference numeral 15 and transfer drive 16. The chassis 10 also accommodates an input drive 18 of a telescopic piston rod assembly for applying an axial force to a bung 20 (see FIG. 2) of the medicament cartridge and which will be described in more detail below with reference to FIGS. 4-8. The gear train comprises a motor pinion 21 and three compound gear stages 22, 23 and 24. The motor pinion 21 is retained on a shaft of the motor 13 with an interference fit and has a pair of moulded flags 25 disposed at 180 degrees about the motor pinion 21. The motor pinion 21 and each compound gear stage 22 to 24 serves to reduce the rotational speed of the drive between the motor 13 and the transfer drive 16 in a ratio of, for example, 124:1 so that for every revolution of the input drive 18, the motor rotates 124 times. The gear train 15 ratio is thus created through five stages. The compound reduction gear stages 22 to 24 are mounted on two parallel stainless steel pins.

Figure 4:
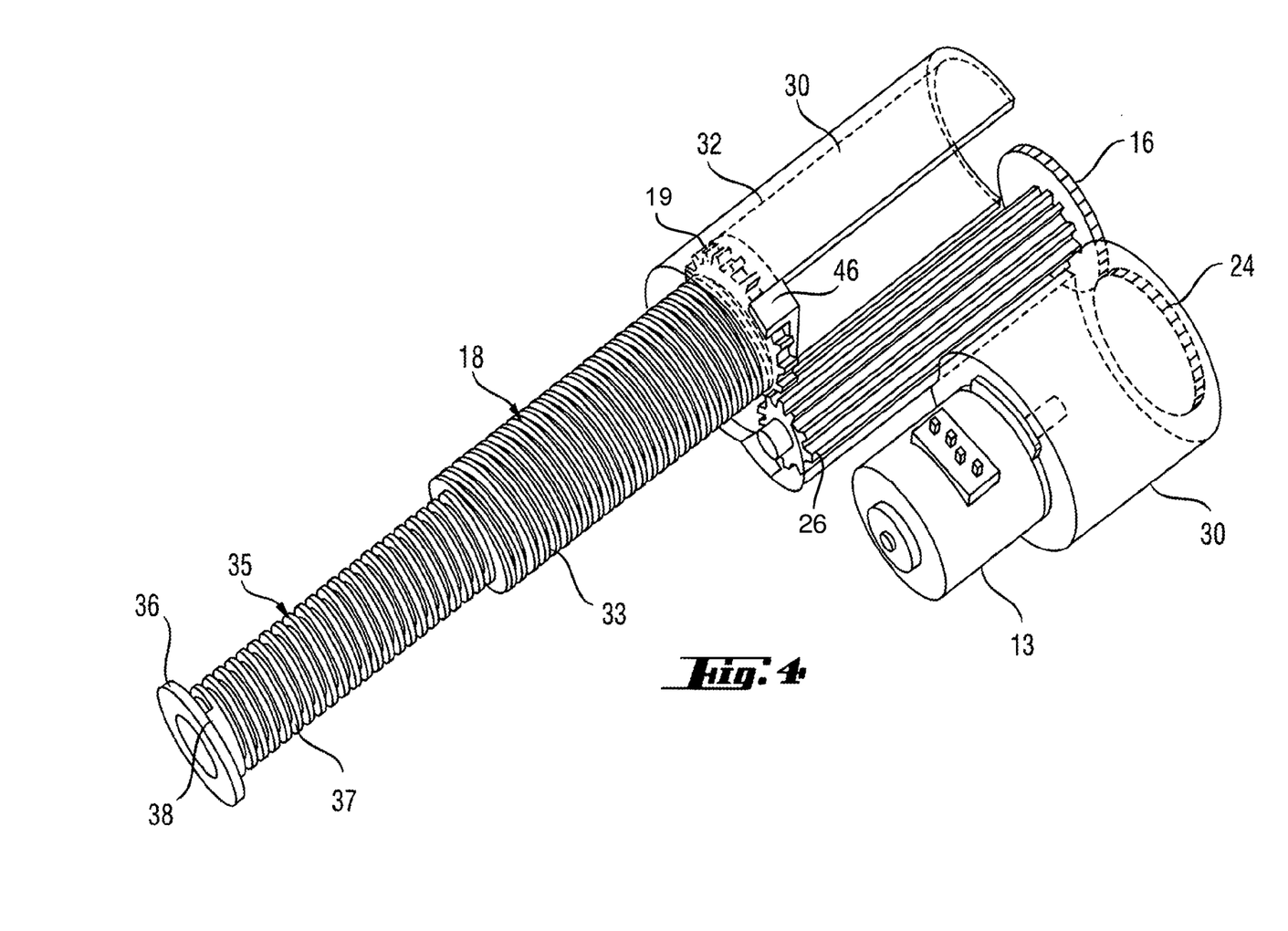
FIG. 4 is a perspective schematic view of the telescopic piston rod assembly in an extended position.

FIG. 4 shows a perspective schematic view of part of the medicament delivery device 1 with the telescopic piston rod assembly in an extended position. A drive mechanism housing 30 contains the gear train 15. For clarity, part of compound gear 24 has been shown to illustrate the relative connection between the transfer drive 16, input drive 18 and the gear train 15. The drive mechanism housing 30 additionally accommodates a latch barrel 32 and the transfer drive 16. Although described as an integral component the drive mechanism housing 30 may be formed from several components supported within the chassis 10, dependent upon materials and methods used for manufacture. The latch barrel 32 is axially fixed to the drive mechanism housing 30 and permitted to move through a predefined angular deflection.

As may be seen in FIG. 4, input drive 18 telescopically projects from the latch barrel 32. Input drive 18 comprises a cylindrical barrel with at a screw-type thread 33 that couples to a corresponding nut 41 (see FIG. 5) formed in a wall 42 of the latch barrel 32. The mating of these threads 33, 41 allow the input drive 18 to move both axially and rotationally with respect to the latch barrel 32.

The input drive 18 also telescopically accommodates a plunger 35 via a threaded engagement between threads 37 and the threaded interior end of the input drive 18. The screw thread 37 terminates in an end stop 38. The plunger 35 is also configured to act upon the bung 20 of the medicament cartridge 9 via a disk-shaped foot 36 at the distal end that has a larger cross-sectional area than the majority of the plunger 35 and is adapted to be accommodated within a standard medicament cartridge 9. The foot 36 is moulded to the plunger 35 for example via injection moulding or as a one-piece metal part. The proximal end of the input drive 18 is also provided with a drive gear 19 for meshing with an axially extending gear 26 of the transfer drive 16.

Figure 5:
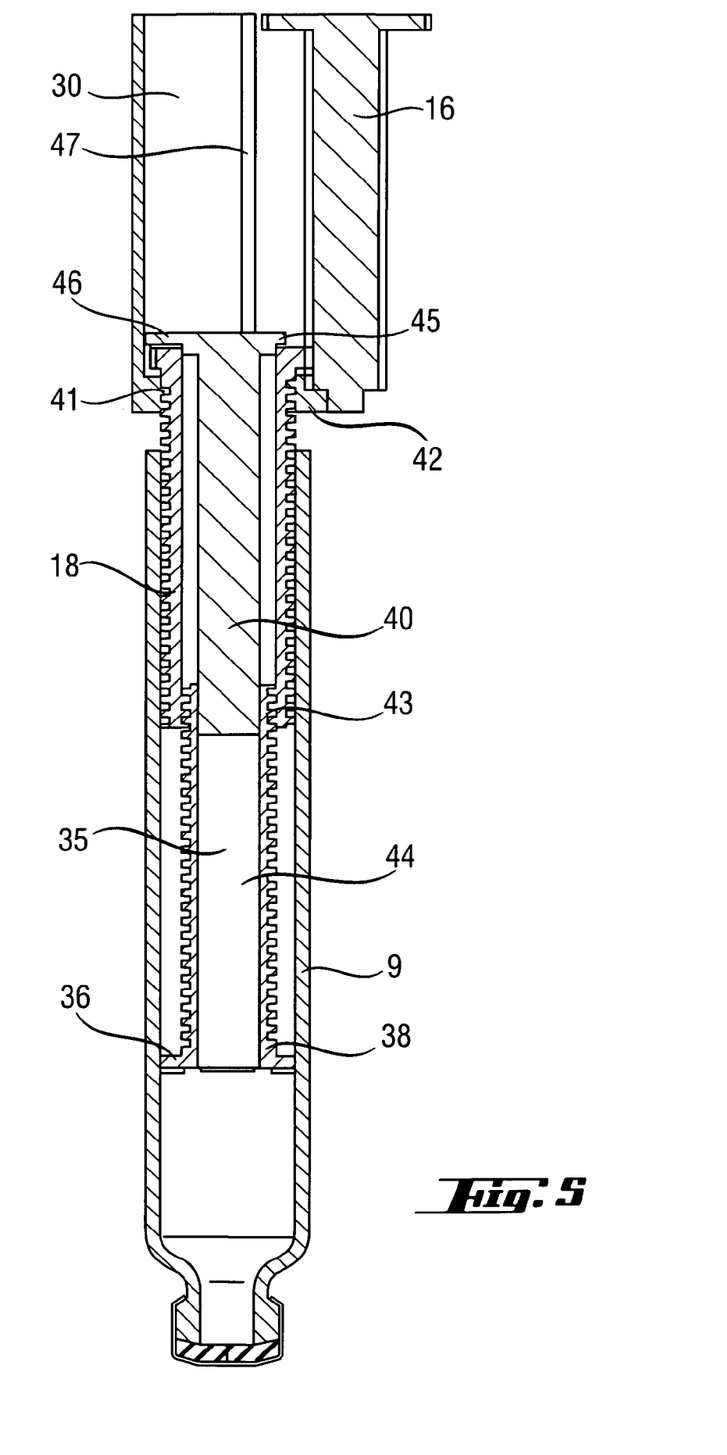
FIG. 5 is a sectional view of the telescopic piston rod assembly of FIG. 4.

FIG. 5 is a cross-sectional view of the piston rod assembly of FIG. 4. In addition to the components described above, FIG. 5 shows in greater detail the threaded engagement 42 between the input drive 18 and the latch barrel 32 and the threaded engagement 43 between the input drive 18 and the plunger 35. FIG. 5 additionally shows a key 40 that is located within the telescopic piston arrangement 18, 35. The key 40 is generally cylindrical and extends through input drive 18. The key 40 has a D-shaped cross-section that is accommodated within a correspondingly shaped interior 44 of the plunger 35, preventing the key from rotating relative to the plunger 35. The key additionally features a flange 45 at its proximal end that abuts the proximal end of the input drive 18 when the telescopic piston rod is in the elongated position shown in FIGS. 4 and 5. A tab 46 extends from the flange and extends over the input drive 18. The tab 46 may run within a groove 47 within the latch barrel 32 to form an engagement means, preventing relative rotational movement between the barrel 32 and the key 40. This also rotationally locks the key 40 and therefore the plunger 35 with respect to the drive mechanism housing 30 and the chassis 10. The tab 46 also prevents the key 40 and input drive 18 from disengaging as drive 18 moves along the transfer drive 16. It may be appreciated that any male to female engagement means can be utilised to achieve a similar effect.

Figure 6:
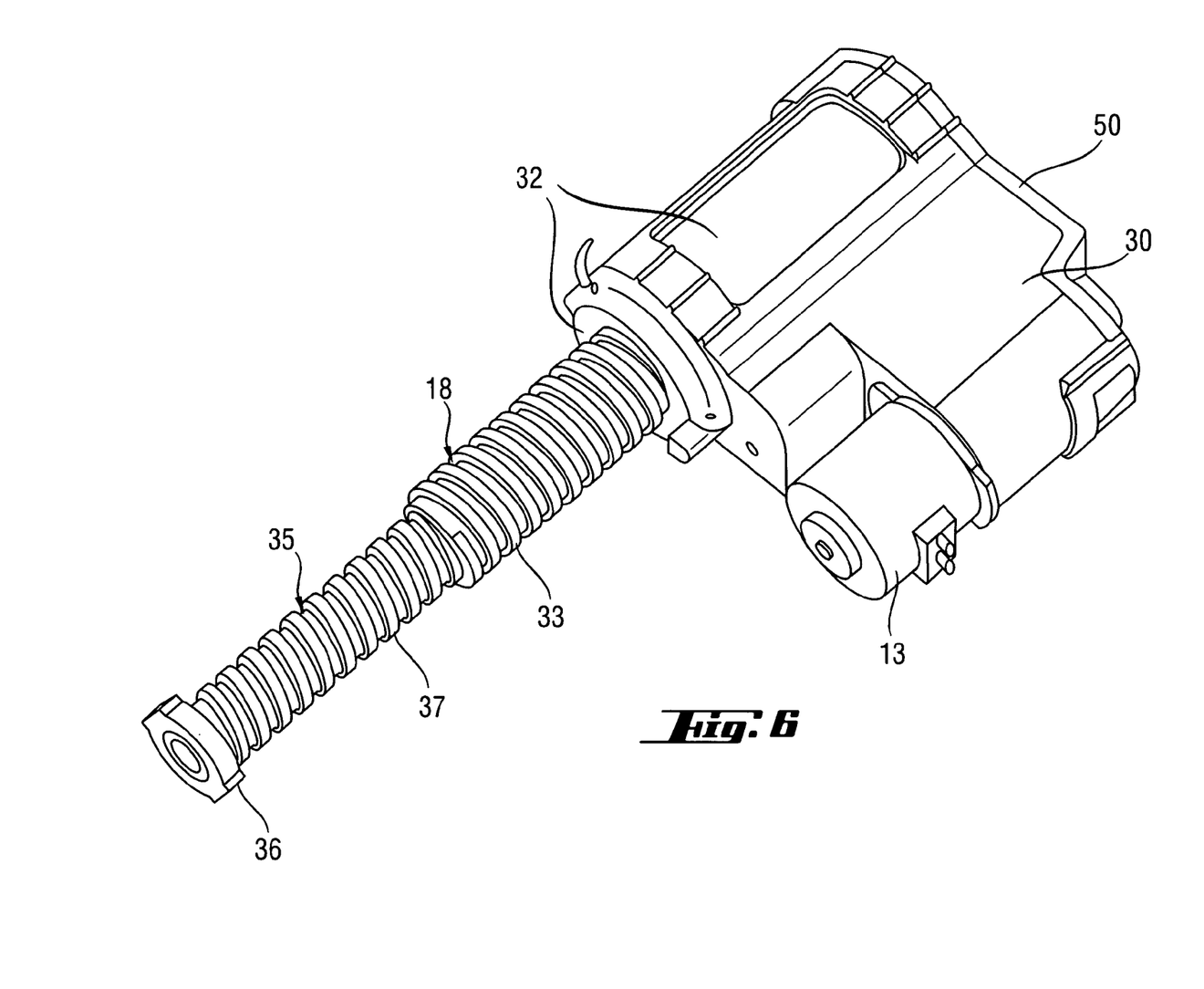
FIG. 6 is a perspective view of a telescopic piston rod and drive mechanism housing embodying the present invention.
Figure 7:
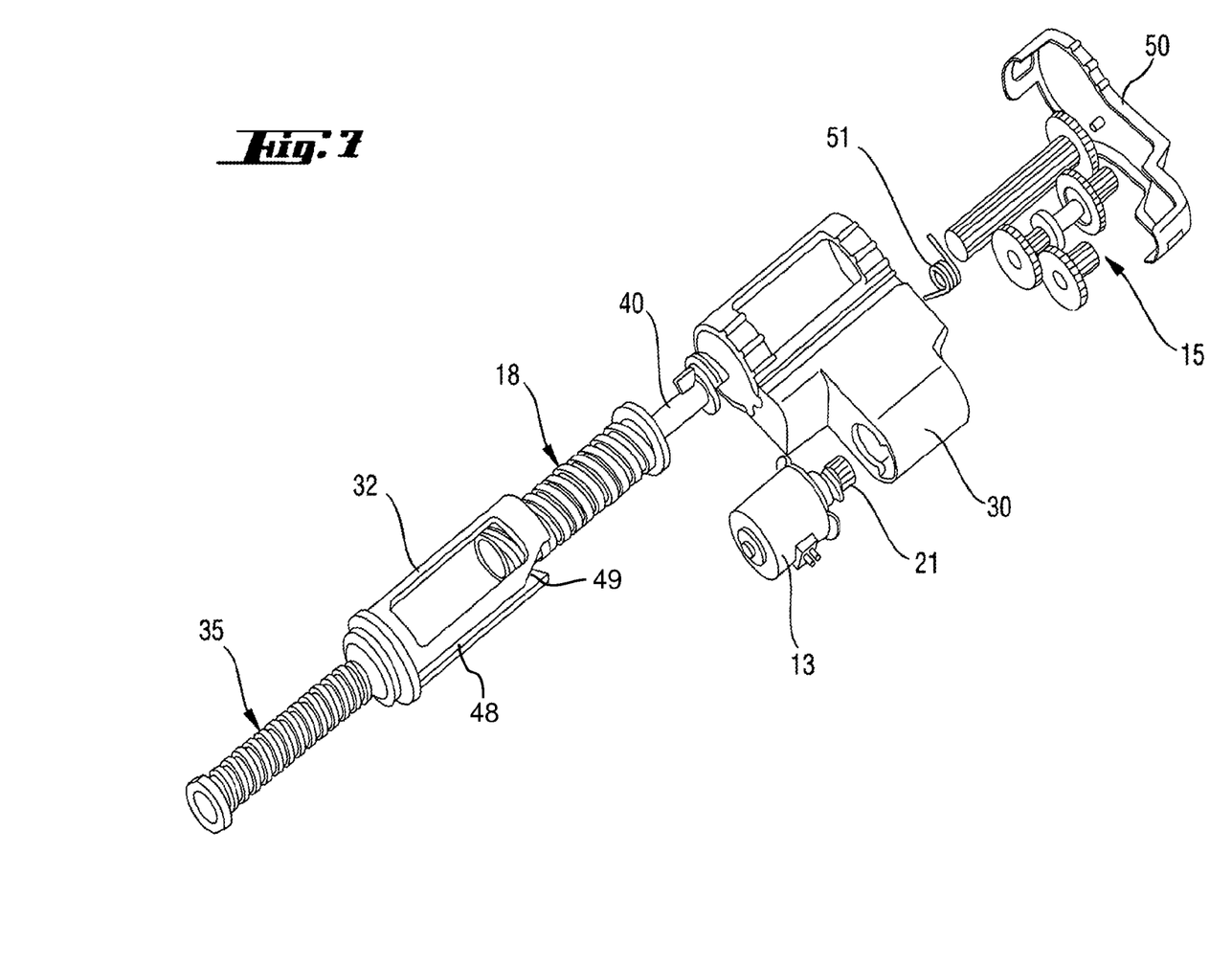
FIG. 7 is an exploded view of the device of FIG. 6.

FIG. 6 shows a three quarter view of the telescopic piston rod assembly 18, 32, 35 and the drive mechanism housing 30, 31 with the piston rod assembly in the extended position and FIG. 7 shows an exploded view of the medicament delivery device 1 of FIG. 6. The figures illustrates how the piston rod assembly 18, 32, 35 is housed within the drive mechanism housing 30 and additionally shows the provision of a gearbox cover 50 that abuts the gear train 15 and snap-fits to the drive mechanism housing 30. A torsion spring 51 is additionally provided to bias the latch barrel 32. FIG. 7 also illustrates that a first portion 48 of the groove 47 is disposed parallel to the axially extending gear and a second portion 49 of the groove 47 is disposed non-parallel to the axially extending gear. When the key is located in the second portion 49, the key moves axially and rotationally according to a skew of the groove 47.

Figure 8:
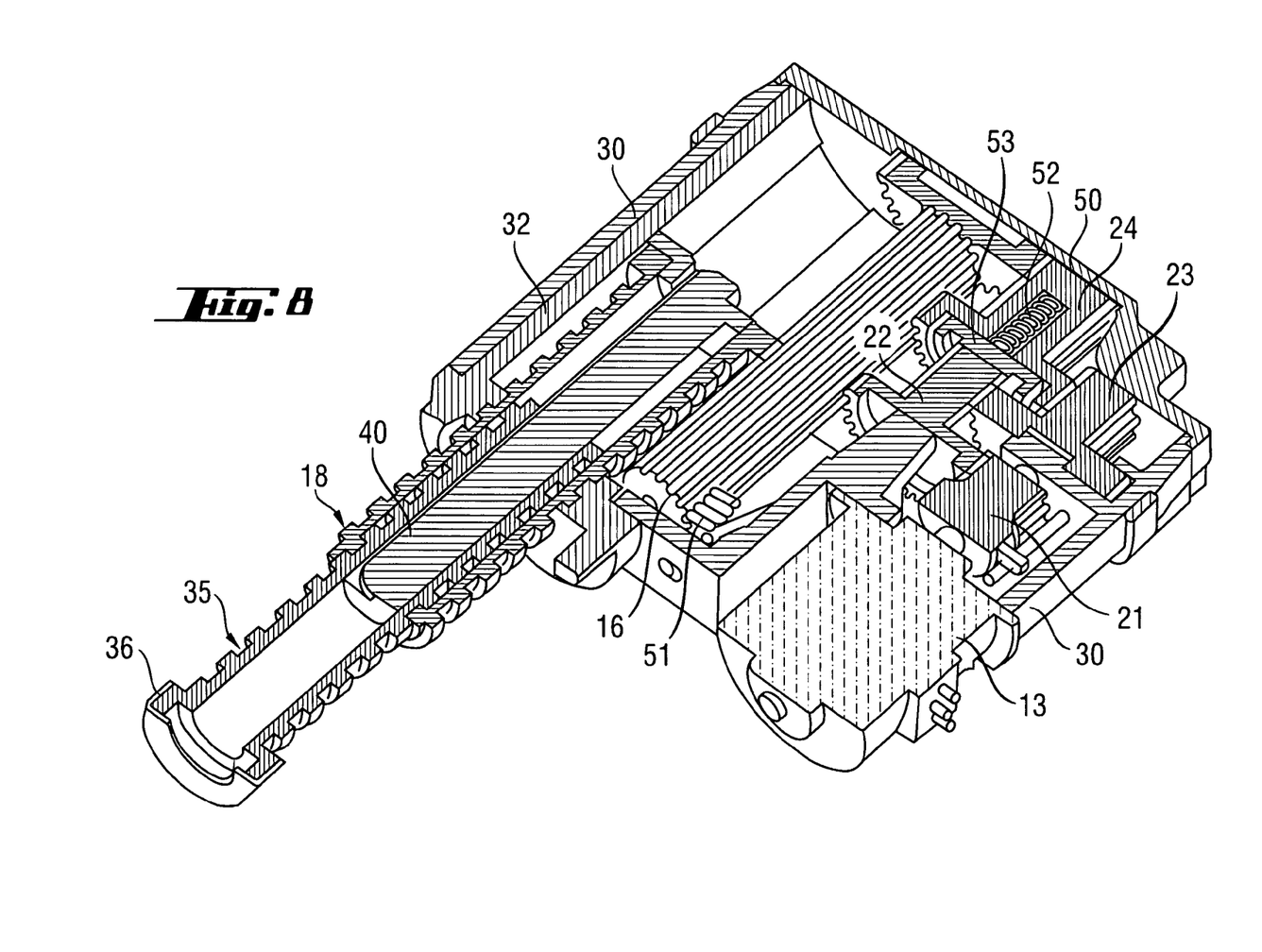
FIG. 8 is a sectional view showing the device of FIG. 6 in a part extended position.
Figure 9:
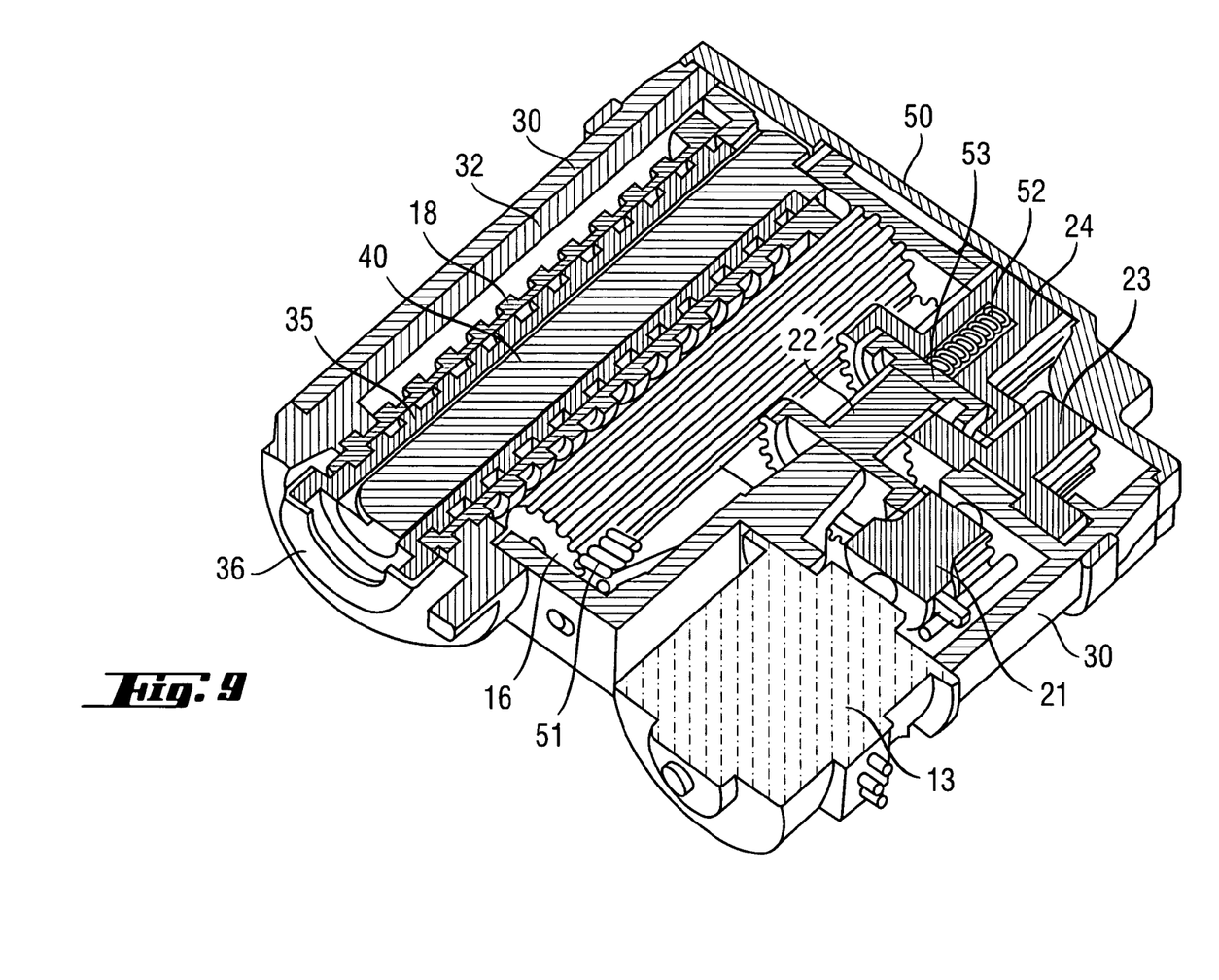
FIG. 9 is a sectional view showing the device of FIG. 9 in a retracted position.

FIGS. 8 and 9 show cross-sectional views of the medicament delivery device 1 in FIG. 6, with the piston rod assembly 18, 32, 35 shown in a part-extended position and retracted position respectively. In addition to the components described above, a spring 52 is shown within gear 24 that acts with flange 53 to reduce noise or 'chatter' within the gear train 15. The spring 52 biases the flange 53 against the gear 22 to reduce chatter.

Operation of the medicament delivery device in accordance with the present invention will now be described.

Initially, the medicament delivery device 1 is in the state shown in FIGS. 1 and 9, with no ampoule loaded and the piston rod assembly 18, 32, 35 in the fully retracted position. After an ampoule 9 has been loaded into the medicament delivery device 1 via the tilting of door 7 (FIG. 2), and a needle attached to the needle attachment 8, the medicament delivery device is ready to use. A user may then, using the input buttons 4, 5, 6 and display 3, prime the medicament delivery device 1 and perform additional operations, for example setting a dose.

The medicament delivery device 1 includes an electronic control system (not shown) for controlling the operation of the medicament delivery device. The control system is operative for controlling the motor 13 to drive the input drive 18 via the gear train 15. Sensors (not shown) are provided for sensing the state of the telescopic piston rod assembly 18, 32, 35 and providing the user with operational information.

In the fully retracted position, the plunger 35 is accommodated within the input drive 18. The input drive 18, in turn, is also housed within the latch barrel 32. The key 40 is also located within the plunger 35 and lies adjacent to the transfer drive 16 with the proximal end of the key 40 additionally lying adjacent to the gear box cover 50.

To administer a dose a user instructs the medicament delivery device 1 to begin injection according to the relevant procedure. This initiates the motor 13 which acts to turn the drive train 15. Specifically, the motor 13 turns motor pinion 21 that is coupled to the gear 22, causing it to rotate. The rotation of the gear 22 in turn causes the gear 23 to rotate, which causes the gear 24 to also rotate. All of the gears are engaged via standard toothed coupling as well known in the art. The final gear stage 24 acts upon the transfer drive 16 via the rotational coupling between the gearing elements. As the transfer drive 16 rotates, meshing with the drive gear moulded to the end of the input drive 18 opposite to the threaded engagement with the plunger 35 causes the input drive 18 to rotate.

As the input drive 18 rotates, the threaded engagement 42 between the input drive 18 and the latch barrel 32 causes the input drive 18 to rotate and telescopically unwind relative to the drive mechanism housing 30 and the latch barrel 32. As the latch barrel 32 is keyed with respect to the input drive 18, the input drive 18 moves axially and rotationally away from the latch barrel 32. Due to the coupling between the key 40, the latch barrel 32, the input drive 18 and the plunger 35; as the input drive 18 moves axially and rotationally, the key 40, prevented from rotating due to the coupling to the latch barrel 32, is forced to move axially due to the tab 46 coupling between the key 40 and the proximal end of the input drive 18.

The rotational and axial movement of the input drive 18 is translated to the plunger 35 via the threaded engagement 43 between the interior surface of the input drive 18 and the exterior surface of the plunger 35. Additionally, due to the coupling between the D-shaped key 40 and the correspondingly D-shaped interior 44 of the plunger 35, the plunger is rotationally coupled to the key 40 and is therefore fixed rotationally with respect to the key 40 and the latch barrel 32 and drive mechanism housing 30. Consequently, as the input drive 18 rotates the plunger 35 moves axially and telescopically advances relative to the input means. The plunger 35 may then engage the bung 20 to enable the dispensing of medicament through a needle (not shown) on the needle attachment 8.

An intermediate position of the piston rod assembly 18, 32, 35 after continued operation of the motor 13 is shown in FIG. 8. As may be seen, the relative telescopic movement between the plunger 35, input drive 18 and the latch barrel 32 are approximately equal. As the operation of the motor 13 is continued further, the piston rod assembly reaches the fully extended position as shown in FIGS. 4 and 5. In this position, continued rotation of the input drive 18 relative to the plunger 35 and the latch barrel 32 is prevented by a flange on the proximal end of the plunger 35 and a flange on the proximal end of the input drive 18.

In order to retract the piston rod assembly 18, 32, 35, the motor 13 may be run in reverse, causing the input drive 18 and the plunger 35 to telescopically retract into the latch barrel 32 and input means 18 respectively. In addition, the key moves axially with respect to the plunger until the proximal flange of the plunger abuts the flange of the disk shaped flange 45 of the key 40.

The invention claimed is:

1. A medicament delivery device comprising:
   a housing;
   a telescopic piston rod assembly for driving a bung of a medicament container, the telescopic piston rod assembly comprising a plunger for driving the bung, a cylindrical input drive, and an elongate key member positioned within the plunger, wherein the plunger comprises an external screw thread, wherein the cylindrical input drive comprises a distal end and a proximal end, and wherein the proximal end of the cylindrical input drive comprises a drive gear; and
   a drive mechanism for the telescopic piston rod assembly, the drive mechanism comprising a rotatable transfer drive configured to be operatively coupled to the cylindrical input drive for rotating the cylindrical input drive, wherein an outer surface of the rotatable transfer drive comprises an axially extending gear,
   wherein the cylindrical input drive is configured to move axially along the outer surface of the rotatable transfer drive as the cylindrical input drive moves telescopically relative to the plunger,
   wherein the external screw thread of the plunger engages with an internal screw thread of the cylindrical input drive at the distal end of the cylindrical input drive, so that rotation of the cylindrical input drive telescopically retracts or expands the plunger relative to the cylindrical input drive, and
   wherein the drive gear meshes with the axially extending gear of the rotatable transfer drive, so that as the cylindrical input drive is rotated by the rotatable transfer drive, the drive gear slides along the axially extending gear relative to the housing.

2. A medicament delivery device according to claim 1, wherein the key allows a predetermined amount of rotational movement.

3. A medicament delivery device according to claim 1, wherein the cylindrical input drive is provided with an external screw thread that engages with and passes through a correspondingly screw threaded opening provided in the housing.

4. A medicament delivery device according to claim 1, wherein the key comprises an elongate member that non-rotationally extends into a first end of the plunger opposite from a second end thereof that drives the bung of the medicament container.

5. A medicament delivery device according to claim 4, wherein the key extends through the cylindrical input drive such that a proximal end of the key extends into the housing to lie substantially adjacent the axially extending gear of the rotatable transfer drive.

6. A medicament delivery device according to claim 5, wherein the proximal end of the key is provided with a tab or projection that extends over the drive gear of the cylindrical input drive and into a corresponding recess or guide provided on or in the housing.

7. A medicament delivery device according to claim 6, wherein at least a portion of the corresponding recess or guide is disposed parallel to the axially extending gear so that as the cylindrical input drive is rotated, the key moves axially in parallel for at least part of a length of the axially extending gear.

8. A medicament delivery device according to claim 5, wherein at least a portion of the corresponding recess or guide is disposed non-parallel to the axially extending gear so that as the cylindrical input drive is rotated, the key moves axially and rotationally according to a skew of the recess or guide.

9. A medicament delivery device according to claim 1, wherein the drive mechanism comprises a device for reducing noise and/or reducing tolerances within the drive mechanism.

10. A medicament delivery device according to claim 1, wherein the housing includes a receptacle for a user replaceable medicament cartridge.

11. An auto-injector including a medicament delivery device according to claim 1.

* * * * *